US012148080B2

(12) United States Patent
Du et al.

(10) Patent No.: US 12,148,080 B2
(45) Date of Patent: Nov. 19, 2024

(54) METHOD FOR LOCATING A CENTER OF ROTATION OF AN ARTICULATED JOINT

(71) Applicant: DASSAULT SYSTEMES, Velizy Villacoublay (FR)

(72) Inventors: Xia Du, Velizy Villacoublay (FR); Pinghan Chen, Velizy Villacoublay (FR); Mickael Brossard, Velizy Villacoublay (FR); Sarath Reddi, Bengaluru (IN)

(73) Assignee: DASSAULT SYSTEMES, Velizy Villacoublay (FR)

( * ) Notice: Subject to any disclaimer, the term of this patent is extended or adjusted under 35 U.S.C. 154(b) by 666 days.

(21) Appl. No.: 17/163,201

(22) Filed: Jan. 29, 2021

(65) Prior Publication Data
US 2021/0248802 A1 Aug. 12, 2021

(30) Foreign Application Priority Data

Feb. 6, 2020 (EP) .................................... 20305112

(51) Int. Cl.
*A61B 5/00* (2006.01)
*A61B 5/103* (2006.01)
*G06T 3/10* (2024.01)
*G06T 13/40* (2011.01)
*G06V 40/20* (2022.01)
*A61B 34/10* (2016.01)

(52) U.S. Cl.
CPC .............. *G06T 13/40* (2013.01); *A61B 5/103* (2013.01); *A61B 5/4528* (2013.01); *A61B 5/6828* (2013.01); *G06T 3/10* (2024.01); *G06V 40/23* (2022.01); *A61B 2034/105* (2016.02)

(58) Field of Classification Search
None
See application file for complete search history.

(56) References Cited

U.S. PATENT DOCUMENTS

| 5,604,856 A | * | 2/1997 | Guenter | .................... | G06T 5/50 |
| | | | | | 345/473 |
| 2004/0106861 A1 | | 6/2004 | Leitner | | |
| 2005/0113720 A1 | | 5/2005 | Cinquin et al. | | |

(Continued)

OTHER PUBLICATIONS

Extended Search Report issued Aug. 25, 2020 in Europe Patent Application No. 20305112.3-1218, 10 pages.

*Primary Examiner* — Joni Hsu
(74) *Attorney, Agent, or Firm* — Oblon, McClelland, Maier & Neustadt, L.L.P.

(57) ABSTRACT

A method for locating a center of rotation of an articulated joint connecting two bones or set of bones of an upper or lower limb of a user, including performing a series of repetitive movements of sweeping one of the bones or set of bones around the joint, and simultaneously acquiring 3D positions of the bone or set of bones during said series, thereby obtaining a 3D cloud of points, computing a point referred to as center point, said center point being a searching point of the 3D searching space for which the standard deviation is the lowest considering the set of distances between the searching point and each point of the 3D cloud of points, transforming the 3D cloud of points into a plane, projecting the center point on said plane, thereby obtaining the center of rotation of the joint.

20 Claims, 5 Drawing Sheets

(56) References Cited

U.S. PATENT DOCUMENTS

| | | | |
|---|---|---|---|
| 2006/0228101 A1* | 10/2006 | Sullivan | G03B 15/16 |
| | | | 396/153 |
| 2011/0144704 A1* | 6/2011 | Switzer | A61B 5/0064 |
| | | | 606/86 R |
| 2015/0213653 A1 | 7/2015 | Kord | |
| 2019/0291723 A1* | 9/2019 | Srivatsa | G05D 1/0221 |
| 2020/0005486 A1* | 1/2020 | Sinha | G06T 7/337 |
| 2020/0163718 A1* | 5/2020 | Austin | A61B 5/1121 |

* cited by examiner

METHOD FOR LOCATING A CENTER OF ROTATION OF AN ARTICULATED JOINT

CROSS-REFERENCE TO RELATED APPLICATIONS

This application claims priority under 35 U.S.C. § 119 or 365 to European Application No. 20305112.3, filed Feb. 6, 2020. The entire contents of the above application(s) are incorporated herein by reference.

FIELD

The disclosure pertains to the field of computer programs and systems, and specifically to the fields of digital human modeling, product review, ergonomics analysis and validation, in an immersive environment.

BACKGROUND

In an immersive environment, the user interacts with the 3D scene through a graphical representation, commonly referred to as an avatar. Be it in a first person visualization (the user sees the arm of his avatar but does not see the entire avatar), or in a tierce person visualization (the user sees his avatar), the estimation of the length of the arms of the avatar must be as precise as possible. In particular, in ergonomics validation, a precision of a few millimeters of the limb length is required. For example, for the simulation of a work station having an emergency stop button, the ability of the user to reach it or not, in the immersive environment, is crucial so as to validate the work station.

Therefore, the experience in the virtual immersive environments is meaningful and realistic only when the mapping from the real world onto the virtual world is accurate. This aspect is also pertinent in the scenarios where avatars are used to evaluate the prototypes of modeled objects using virtual reality devices. One of the fundamental requirements in this scenario is the dimensional uniformity of the avatar with its counterpart (human) in the real world. This can be achieved by modifying the avatars dimensions with the dimensions of the human who is guiding the avatar.

SUMMARY

However, modeling the human skeletal structure is complex. A human skeleton can be seen as a group of bones. Articulated joints can be defined as the relative interactions between some of these bones, these interactions comprising rolling, translations and sliding motions of bones. The behavior of these anatomical joints varies from simple fixed axis of rotation to very complex polyaxial coupled motions. For example, considering the scapula-humeral rhythm, the scapula and humerus move in a ½ ratio: when the arm is abducted by 180 degrees, 60 degrees occurs by rotation of the scapula, and 120 degrees by rotation of the humerus at the shoulder point. In the present application, it will be considered that a joint behaves like an axis of rotation. Indeed, a goal of the disclosure is not to determine the real skeleton of a user, but rather to model the length and articulations of a limb. Even with that simplification, accurately capturing and mapping these motions onto digital humans using limited number of tracker is a difficult task.

On the one hand, modeling the human structure can be carried out by arranging magnetic and/or optical markers on adequate locations of the human body. The article "Automatic Joint Parameter Estimation from Magnetic Motion Capture Data" (James F. O'Brien et al., Proceedings of the Graphics Interface 2000 Conference, May 15-17, 2000) discloses a technique for using magnetic motion capture data to determine the joint parameters of an articulated hierarchy. This technique makes it possible to determine limb lengths, joint locations, and sensor placement for a human subject without external measurements. According to table 1 of the article, the disclosed technique is very precise: for the upper arm, the difference between the measured (with a ruler) and the calculated value is equal in average to ⅔ millimeters. However, the technique requires wearing a motion capture harness, equipped with the sensors, which is then useless, for the immersive experiment, once the modeling has been done. Moreover, the accuracy of this kind of solutions is usually inked to the accuracy of the marker positioning; therefore the setup cannot be done alone (it is usually carried out by an expert), which is costly and takes a lot of time.

On the other hand, bone length estimation using markerless tracking systems are less accurate when compared to marker based systems. Markerless systems can be found in consumer grade virtual reality systems, for example for video games applications. In that case, the user inputs his size, and the length of the upper limbs is derived based on statistical considerations. However, there is no real proportionality between the size and the length of the limbs, a tall person may have short arms, and inversely. Thus, the technique is not accurate.

Therefore, there is a need for providing a quick and accurate markerless method for modeling the human upper or lower limbs of a user for an immersive environment application, in particular for locating the centers of rotation of articulated joints connecting bones of the upper or lower limb, and also for estimating the dimensions of the upper or lower limb.

An object of the present disclosure is a method for locating a center of rotation of an articulated joint connecting two bones or set of bones of an upper or lower limb of a user, comprising the steps of:
  a) performing, by the user, a series of repetitive movements of sweeping one of the bones or set of bones around the joint, and simultaneously acquiring 3D positions of the bone or set of bones during said series, thereby obtaining a 3D cloud of points;
  b) computing, in a 3D searching space comprising a 3D position of a termination of the other bone or set of bones, a point referred to as center point, said center point being a searching point of the 3D searching space for which the standard deviation is the lowest considering the set of distances between the searching point and each point of the 3D cloud of points;
  c) transforming the 3D cloud of points into a plane;
  d) projecting the center point on said plane, thereby obtaining the center of rotation of the joint.
In an embodiment:
  the method comprises a preliminary step of providing two hand-held backers
  in step a), the series of repetitive movements are performed while holding one of the hand-held trackers, referred to as mobile tracker, the other hand-held tracker, referred to as reference tracker, being maintained against the termination of the other bone or set of bones.

In an embodiment, step b) comprises the subs-steps of recursively subdividing the 3D searching space by:

b1) defining the 3D searching space as a cube of predefined edge length, and which is centered on the 3D position of the reference tracker, referred to as reference point;

to b2) receiving, from a user, an input identifying a set of points of the cube constituting, with said reference point, a set of searching points;

b3) for each searching point, computing the distance between said searching point and each point of the 3D cloud of points, and deriving a standard deviation for each searching point b4) identifying, among the set of searching points, at least one searching point, for which standard deviation is the lowest, b5) reiterate steps b1), b2), b3) and b4) by also halving the edge length of the cube and centering the cube on the identified searching point, until the edge length of the cube is lower or equal to a predefined threshold, the center point corresponding then to the identified searching point.

In an embodiment, in step b2), the cube is subdivided into eight smaller cubes, and the set of searching points comprises the reference point or the identified searching point, the small cites centers, the centers of squares of two adjacent smaller cubes, and the middle points of the edge of two adjacent smaller cubes.

In an embodiment, step c) comprises the sub-steps of:
c1) computing a covariance matrix of points of the 3D cloud of points;
c2) computing eigenvalues and eigenvectors of the covariance matrix;
c3) constructing a rectangular bounding box enclosing the 3D cloud of points, the orientation of the bounding box corresponding to the eigenvectors, the dimensions of the bounding box corresponding to the eigenvalues;
c4) computing the geometry center of the bounding box;
c5) constructing the plane which is defined by the two eigenvectors which have the biggest eigenvalues and which passes through the geometry center of the bounding box.

In an embodiment, in step a), the acquired 3D positions are stored in frames, each frame comprising a predefined number of 3D positions, and steps b), c) and d) are implemented for all the frames whenever a new frame has been acquired.

In an embodiment, the method comprises the steps of:
storing the 3D position of the reference tracker for each implementation of steps a), b), c) and d),
computing a mean of the 3D positions of the reference tracker, and
discarding a corresponding frame if the 3D position of the reference tracker differs from the mean of the stored 3D positions of the reference tracker from more than a predefined value.

In an embodiment, the method comprises discarding a frame if, in step c2), it is determined that there is no single eigenvalue which is smaller than the others.

In an embodiment, the method comprises a step of transmitting in real time to the user an indication of the minimum standard deviation.

The disclosure also relates to a method for estimating the dimensions of the upper limb of a user, comprising the steps of:

S1: computing the length of the hand based on the distance between the computed location of the center of rotation of the wrist with the method according to any of the preceding claims and the location of the origin of the mobile tracker;

S2: computing the length of the forearm based on the distance between the computed location of the center of rotation of the wrist with the method according to any of the preceding claims and the computed location of the center of rotation of the elbow with the method according to any of the preceding claims;

S3: computing the length of the upper arm and forearm based on the distance between the computed location of the center of rotation of the wrist with the method according to any of the preceding claims and the computed location of the center of rotation of the shoulder with the method according to any of the preceding claims;

S4: computing the length between the left and right shoulders based on the length of the upper arm and forearm, the length of the hand, and the maximum distance between the reference tracker and the mobile tracker when each of them are hold in a different hand of the user, and waved in the frontal plane of the user with the arms stretched.

The disclosure also relates to a computer program product, stored on a non-transitory computer-readable data-storage medium, comprising computer-executable instructions to cause a computer system to carry out a method according to any of the preceding claims.

The disclosure also relates to a non-transitory computer-readable data-storage medium containing computer-executable instructions to cause a computer system to carry out the aforementioned method.

The disclosure also relates to a computer system comprising two hand-held trackers, a processor coupled to a non-transitory memory, a screen, the memory storing computer-executable instructions to cause the computer system to carry out the aforementioned method.

BRIEF DESCRIPTION OF THE DRAWINGS

Additional features and advantages of the present disclosure will become apparent from the subsequent description, taken in conjunction with the accompanying drawings, which show.

DETAILED DESCRIPTION

Figure 1:
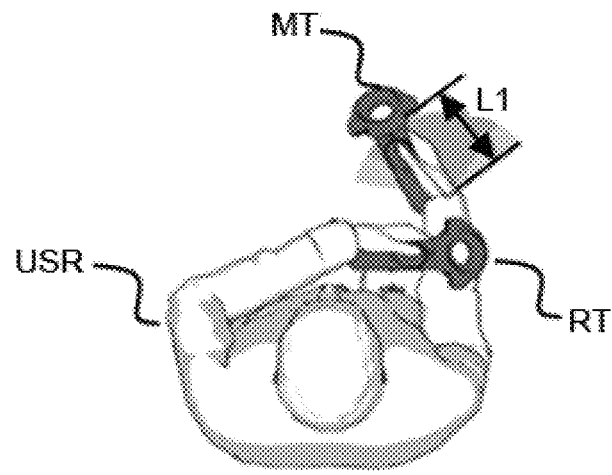
FIG. 1, a top view of a user performing a series of repetitive movements of sweeping his hand.

FIG. 1 illustrates a top view of a user performing a series of repetitive movements of sweeping his hand for determining the center of rotation of the wrist.

In a first step of the invented method, a) the user USR performs a series of repetitive movements of sweeping one of the bones or set of bones around the joint, and simultaneously acquiring 3D positions of the bone or set of bones during said series, thereby obtaining a 3D cloud of points P. The obtained 3D could of points is displayed in FIG. 2.

In an embodiment, which is particularly suitable for locating the center of rotation of the wrist of the user, the user USR holds a tracker (MT, RT) in each hand.

The trackers (MT, RT) may be part of a virtual reality system, for example the "HTC Vive"™ virtual reality system. Such a system comprises at least one hand-held tracker (wireless handheld controller), a virtual reality headset for displaying a 3D scene to the user in an immersive context. The implementation of the invented method does not require the use of a virtual reality headset, since the claimed method is not directed to the immersive experiment itself, but rather to the prior calibration of the avatar of the user. Besides, two hand-held trackers are used, i.e. one for the left upper/lower limb, and one for the right upper/ow limb. Therefore, no expensive motion capture system is required.

The trackers may be located in the coordinate system of the virtual environment in different ways: through cooperating with base stations, by surface detection, markers, environmental recognition, gyroscopic control units, computer vision. For the invented method, the position of the origin of each of the tracker is known with one those techniques.

The trackers am not necessarily dedicated to virtual reality, provided that a 3D position can be determined. The trackers may be used only for the calibration process.

In this embodiment, the hand-held trackers (MT, RT) are identical. The tracker which is held by the hand making repetitive movements of sweeping the set of bones of the hand around the wrist is referred to as the mobile tracker MT, whereas the other tracker is referred to as the reference tracker RT.

The estimation of the position of the center of rotation may be computed once all the 3D positions of the bone or set of bones have been obtained. Alternatively, the estimation could be computed whenever a predefined number of points has been obtained, hereafter referred to as a frame. Therefore, a real time estimation of the position of the center of rotation can be carried out, depending of the hardware of the trackers, and also depending on the virtual reality software. For example, the hand-held trackers of the "HTC Vive"™ virtual reality system have a refresh rate which can be up to 90 Hz. In order to enhance the real time visual rendering, the refresh rate can be set up at a much lower value than 90 Hz. In the claimed method, the 3D positions of the mobile tracker MT are stored in frames of predefined length (for example 25 points), and the position of the center of rotation is computed firstly for the first frame, then for the two first frames (for example 50 points), then for the three first frames (for example 75 points), and so on. Therefore, the user feels a near-real time measure, and the accuracy of the measures increases with the time.

In order to locate the center of rotation of the wrist, the user USR holds the mobile tracker MT and the reference tracker RT in the hands. While keeping the reference tracker RT stable and close to the wrist, the user waves the mobile tracker MT from the left to the right and inversely, a plurality of times, as illustrated by FIG. 1.

The reference tracker RT has three functions. Firstly, as it will be described below, it provides a first estimation of the location of the center of rotation of the wrist, since the user is prompted to keep the reference tracker RT on the forearm, close to the wrist (but not on the wrist, otherwise the measuring process would be noisy). Secondly, by keeping the reference tracker RT on the forearm, the forearm is more stable, therefore the accuracy of the measure is increased. Thirdly, by knowing the position of the reference tracker RT during the calibration process, we can take into account only the relative movement of the mobile tracker MT with respect to the reference tracker RT, and compensate the global movement of forearm. This will increase the stability of the calibration process.

Although the hand can have a wide angular displacement around the center of rotation of the wrist (approximately 130-140°), it is better not to wave the hand until extreme postures such as an articular stop. It is important for the wrist, because at the end of the movement, the user tends to "break" his wrist, i.e. to radically change the plane of the points P. It is also important for the shoulder movement, because if the movement of the shoulder is too wide, the scapula also moves, so the movement tends to be very complex, implying several articulated joints. The user is prompted not to make too wide angular displacements. For example, in FIGS. 1, 5A, 5B and 5C, which illustrate examples of snapshots of a video tutorial intended as a guide for the user, the angular range corresponding to an extreme posture is displayed differently (for example a different color) than the range corresponding to a desired posture.

The user USR may be prompted, through visual indication on a screen, to arrange his arms as illustrated by FIG. 1. Such a movement is easy to do, even for non-expert users.

In a second step b) of the claimed method, a point referred to as center point Pc is computed in a 3D searching space comprising a 3D position of a termination of the other bone or set of bones. The center point Pc is a point of the searching space which minimizes the standard deviation considering the set of distances between the searching point and each point of the 3D cloud of points.

The 3D searching space firstly comprises the 3D position of the termination of the other bone or set of bones (the termination of the forearm which is close to the wrist, according to the example of FIG. 1). Therefore, by inciting the user to lay the reference tracker RT close to the articulated joint, the stability is increased (because there is less movement of the limb, except for the waving bones or set of bones), and the computation of the center point Pc starts with a point which is close to the real center of rotation, thereby increasing the speed of the method.

Then, in order to find the approximate center of the 3D could of points P, which looks like a bunch of arc shaped points, the method starts from a reference point Porg, to find, at the end, a point in its neighborhood which minimizes the standard deviation considering the set of distances between the searching point and each point of the 3D cloud of points.

Figure 4:
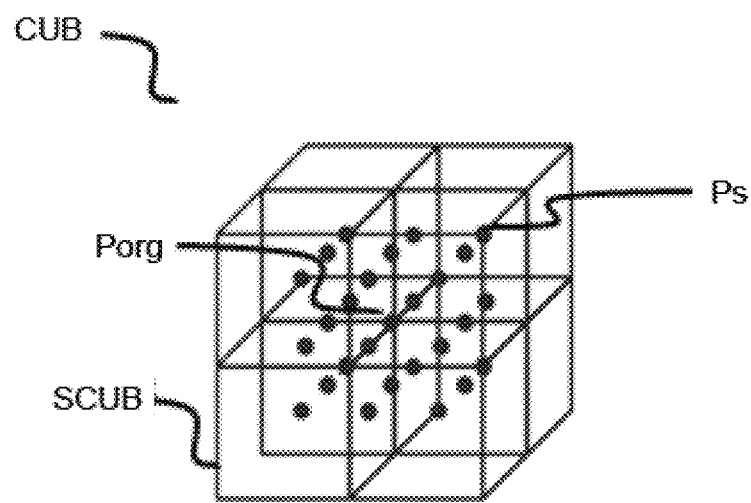
FIG. 4, an illustration of the cube, comprising the searching points.

In an embodiment, the center point Pc is computed based on a octree search algorithm, in which the 3D searching space is recursively subdivided, which comprises the following sub-steps of step b):

In a first sub-step b1), the 3D searching space is defined as a cube CUB of predefined edge length, and which is centered on a reference point Porg which corresponds to the 3D position of the reference tracker RT. FIG. 4 illustrates schematically the cube CUB. For example, the initial predefined edge length may be equal to a few decimeters, so as to be adapted to all the kind of articulations of the upper limb. Indeed, the largest distance between the center of rotation of the articulated joint and the mobile tracker is directed the measure of the length of the entire arm, which is approximately fifty centimeters long, depending of course on the user. In order to measure the positions of centers of rotation of the lower limb (ankle, knee or hip), an initial predefined edge length may be equal to one meter, for the same reasons. The initial predefined edge length may be for example equal to $2^g=512$ mm, which is a good tradeoff considering performance and precision reasons.

Then, in a second sub-step b2) a set of points of the cube CUB are identified. This set of identified points constitutes, with the reference point Porg, a set of searching points Ps. The identified points are, for example, form a network of points which are positioned around the reference point Porg, in a periodical arrangement.

In an embodiment, the cube CUB is subdivided into eight smaller cubes SCUB (voxels), and the set of searching points Ps comprises the following points, for the first iteration of step b):
- the reference point Porg, located at the center of the cube CUB;
- the eight small cube centers;
- the twelve centers of squares of two adjacent smaller cubes SCUB; and
- the six middle points of the edge of two adjacent smaller cubes SCUB.

Another choice of searching points can be made; however, it was found that using those points provides a good result in terms of computing speed.

Then, in a third sub-step b3), for each searching point Ps of the cube CUB, the distance between the searching point Ps and each point of the 3D cloud of points P is computed. It is understood that, when the method is implemented as the frames of 3D points are obtained, the distance between the searching point Ps and the points of the 3D cloud of points P is computed only for the acquired 3D points.

Assume that at time t, N points have been acquired, and that there are Nps searching points. For each searching point Ps of the cube CUB, N distances are computed. For this set of N distances, a standard deviation is computed. For the Nps searching points Ps, Nps standard deviations are computed.

Then, in a fourth sub-step b4), at least one searching point Ps, for which standard deviation is the lowest, is identified. The searching point(s) having the lowest standard deviation(s) indicates, by definition, that the distances between the searching point and each of the points of the 3D could of points P tend to be close to the mean of the distances.

Then, steps b1), b2), b3) and b4) are reiterated. Instead of centering the cube CUB at the reference point Porg (corresponding to the position of the reference tracker RT), the cube CUB is centered at the searching point Ps, for which the standard deviation is the lowest (referred to as identified searching point). For each new iteration, the edge length of the cube CUB is halved.

In an embodiment, in sub-step b4), two searching points having the lowest standard deviations are identified, and the iteration is made in parallel for both points. Therefore, after each iteration, the number of identified searching points doubles. If only one searching point is identified after each iteration, defining more than twenty-seven searching points Ps improves the accuracy of the method.

In any case, be it with one identified searching point at each iteration, or with more than one identified searching point at each iteration (for example two identified searching points), once the edge length of the cube is lower or equal to a predefined threshold, the iteration continues, a single searching point is identified after each iteration. For example, the threshold may be equal to 16 mm.

Then, the iteration is stopped if the edge length of the cube is lower or equal to another predefined threshold, for example 2 mm. The center point Pc is located in the cube CUB whose edge length is lower or equal to 2 mm. Therefore, in that case the resolution is equal to 1 mm (the searching point of the last iteration is in the center of the cube which has an edge length of 2 mm), which is a high resolution compared to the aforementioned methods.

The result of step b), and in an embodiment the result of the octree search, is the center point Pc.

Alternatively, instead of computing the center point Pc based on an octree search algorithm (of logarithmic complexity), the center point Pc can be computed based on a brute force linear search (of near complexity).

Then in a third step c), the 3D cloud of points P is transformed into a plane. The goal of step c) is to map the 3D cloud of points P in two dimensions, while losing too much information.

In an embodiment, the transformation from 3D to 2D is carried on by using the statistical procedure called «Principal component analysis», which is described below.
  c1) computing a covariance matrix of points of the 3D cloud of points (P);
  c2) computing eigenvalues and eigenvectors of the covariance matrix;
  c3) constructing a rectangular bounding box enclosing the 3D cloud of points P, the orientation of the bounding box corresponding to the eigenvectors, the dimensions of the bounding box corresponding to the eigenvalues;
  c4) computing the geometry center of the bounding box;
  c5) constructing the plane which is defined by the two eigenvectors which have the biggest eigenvalues and which passes through the geometry center of the bounding box. It is assumed that the user follows the procedure which is displayed on the screen, and performs the sweeping movement properly. The 3D cloud of points P should be almost on the same plane and looks like an arc shape. So normally, one of the eigenvalues which represents the thickness of this cloud of points is a lot smaller than the other two eigenvalues.

The plane can be constructed once the series of repetitive movements has been completed. In an embodiment, the plane is constructed after the acquisition of a frame of predefined length, with all the already acquired frames. Thus, step c) is also implemented in near-real time, and the user can correct his movements if the stability of the construction of the plane is insufficient. In particular, a frame may be discarded if, during step c3), it is determined that the three eigenvalues are very similar, for example based on a tolerance margin. Therefore, the transformation from 3D to 2D is done with a minimal loss of information.

Alternatively, instead of using the «Principal component analysis» method, the plane may be constructed firstly by computing the rectangular bounding box enclosing the 3D cloud of points. Then, a plane which is parallel to both largest faces of the bounding box, and which divides the bounding box in two equal volumes is computed.

In the last step d) of the claimed method, the center point Pc, which has been computed in step b), is projected on plane which has been computed in step c). The projection of the center point Pc corresponds to the position of the center of rotation Pc' of the joint. In a particular embodiment, in which the user holds a mobile tracker MT, the position of the center of rotation Pc' refers to the 3D position relative to the 3D position of the origin of the mobile tracker MT.

Figure 2:
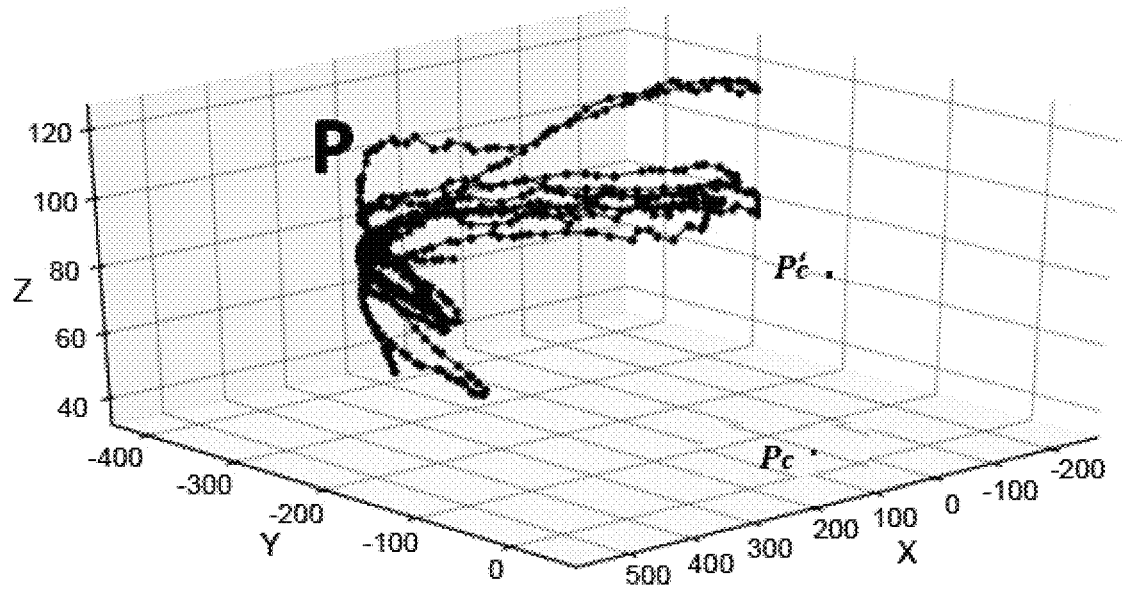
FIG. 2, an illustration of the acquired 3D cloud of points, the computed center point and the computed center of rotation.
Figure 3:
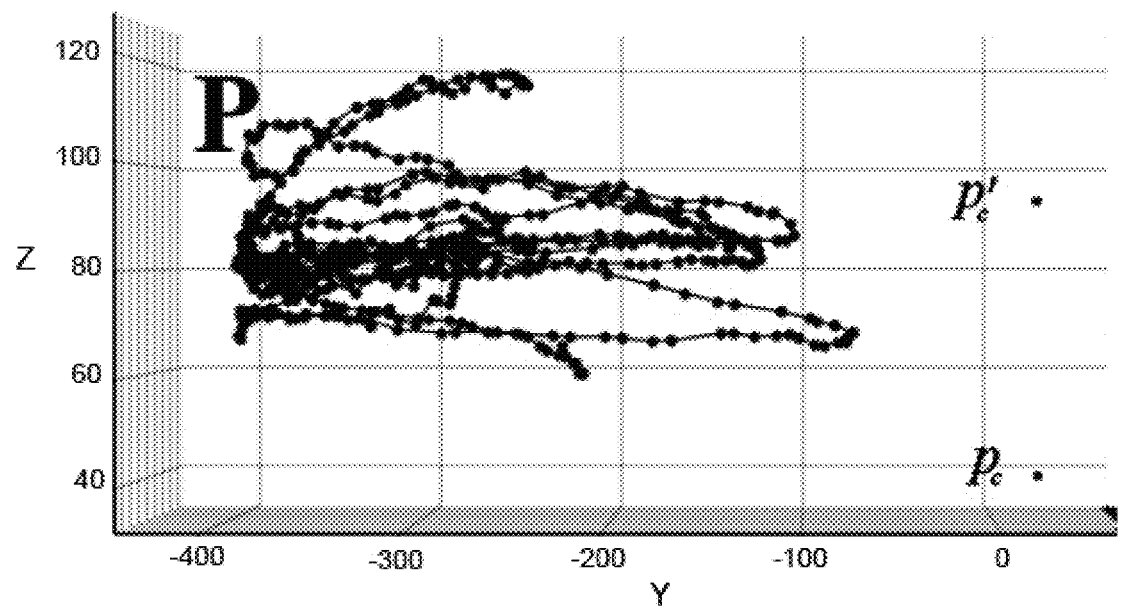
FIG. 3, another illustration of the 3D cloud of points, the center point and the center of rotation.

FIGS. 2 and 3 illustrate the 3D cloud of points P, the center point Pc and the center of rotation Pc'.

In an embodiment, steps a), b), c) and d) are iterated whenever a new frame (comprising twenty-five points, for example) has been acquired. In other words, the position of the center of rotation Pc' is recomputed with all the 3D positions, when a new frame has been acquired. The 3D position of the reference tracker RT is stored in real time, and a mean position of al the stored positions of the reference tracker RT is computed. A new incoming frame is discarded if the 3D position of the reference tracker differs from the mean of the stored 3D positions of the reference tracker from more than a predefined value. Therefore, if the user has moved too much during the series of movements, the 3D position of the reference tracker RT will be unstable, and discarding the corresponding frames avoids computing the center of rotation Pc' for unstable positions of the user.

The distance $d_k$ between the center of rotation Pc' and each of the points of the 3D cloud of points P may be computed. Assuming $Dc=\{d_g, \ldots d_{n-1}\}$ the set of n distances (n=Card (P)). The mean of Dc is the approximate distance between the center of rotation Pc' and the origin of the mobile tracker MT. The length of the bones or set of bones can be easily derived from the approximate distance: by asking the user to press a button of the mobile tracker MT with a specific finger while performing the series of movements, the position of the termination of the finger is known (it corresponds to the position of the pressed button), so the distance between the termination of the finger and the center of rotation Pc' can be computed.

The standard deviation of Dc may be computed in order to estimate the quality of the result. If the standard deviation is too high, the estimation will be untrusted. For example, the quality of result is suggested as acceptable if the standard deviation is under 10 mm, as suspicious if it is between 10 mm and 15 mm, and suggested as bad result if it is over 15 mm. The standard deviation of Dc, or the level of quality (acceptable/suspicious/bad) may be transmitted (displayed) in real time to the user, so that he could correct the current series of movement in order to improve the level of quality. Therefore, the user can see the quality of the measure, through the visual feedback indicating the standard deviation. More generally, the claimed method can be done by the user himself, he does not need to be assisted by an expert person or even by a non expert person.

The inventors empirically tested that for a 3D cloud of approximately 1000 points, a good accuracy of the measure is achieved, provided that the stability criteria is met. With a tracker having a refresh rate of 90 Hz (which is the case for the "HTC Vie"™ virtual reality system), the acquisition is made in approximately 11 seconds. A threshold number of points can be set, for example 1000 points, beyond which the process stops. If the result is very stable, the process may stop before acquiring the threshold number of points.

Figure 5A:
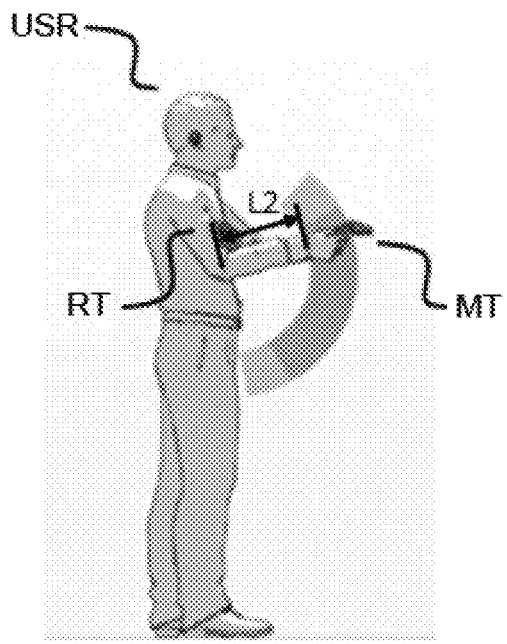
FIG. 5A, a side view of a user performing a series of repetitive movements of sweeping his forearm.
Figure 6:
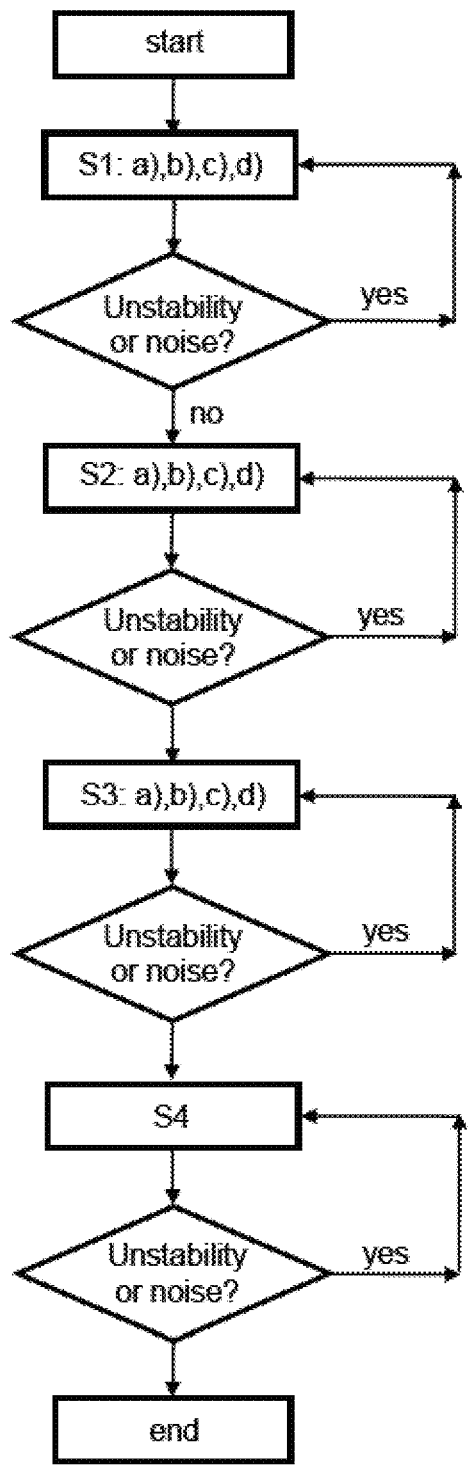
FIG. 6, a flow chart of the method for estimating the dimensions of the upper limb of a user.

In order to estimate the dimensions of the upper limb of a user, the length L1 of the hand is firstly measured with the aforementioned method. It represents step S1 which is lustrated in the flowchart of FIG. 6. The aforementioned steps a)-d) are implemented, and if the measure is stable and not noisy, the same process is implemented for the forearm, in order to compute the center of rotation of the elbow (step S2): the user USR keeps one controller (reference tacker RT) stable and close to the elbow, waves the other controller (mobile tracker MT) by doing a flexion/extension movement and inversely, a plurality of times, as illustrated by FIG. 5A.

Since the position (relative to the origin of the mobile tracker MT) of the center of rotation of the wrist has been previously computed, it is possible to compute the length L2 of the forearm, based on the center of rotation of the elbow and based on the center of rotation of the wrist.

Figure 5B:
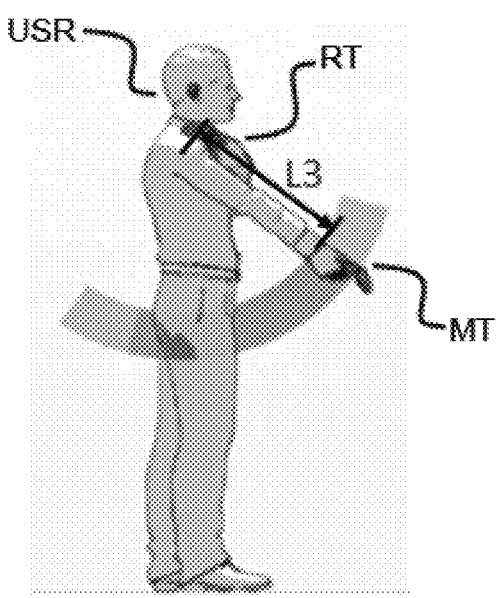
FIG. 5B, a side view of a user performing a series of repetitive movements of sweeping his arm.

The aforementioned steps a)-d) are implemented, and if the measure is stable and not noisy (a noisy measure may happen when the reference tracker RT moves in a wide range, or if the mobile tracker MT does not move in a plane, contrary to the recommendation), the same process is implemented for the forearm, in order to compute the center of rotation of the shoulder (step S3). The same process is implemented for the arm, in order to compute the center of rotation of the shoulder. The user USR keeps one controller (reference tracker RT) stable and close to the shoulder, tries to keep the arm straight, waves the other controller (mobile tracker MT) by the arm up and down and inversely, a plurality of times, as illustrated by FIG. 5B.

Since the position (relative to the origin of the mobile tracker MT) of the center of rotation of the wrist has been previously computed, it is possible to compute the length L3 of the arm (forearm and upper arm), based on the center of rotation of the shoulder and based on the center of rotation of the wrist.

Figure 5C:
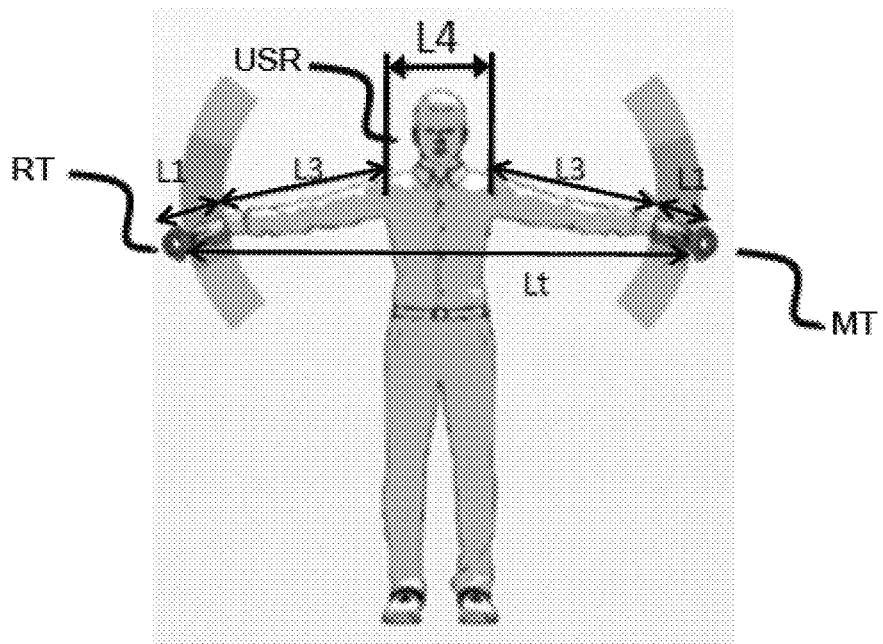
FIG. 5C, a front view of a user performing a series of repetitive movements of sweeping both arms.

Lastly, the length L4 between the left and right shoulders is computed while performing a series of repetitive movements of sweeping both arms stretched, up and down, as illustrated by FIG. 5C. The user USR holds the reference tracker RT in one hand, and the mobile tracker RT in the other. For this step, both trackers are moved.

The length L1 of the hand and the length L3 of the arm are supposed to be identical; thus, the length L1 of the hand and the length L3 of the arm, which have been previously computed for one side, ae considered identical for the other side.

During the series of repetitive movements, the length Lt between the reference tracker RT and the mobile tracker RT is computed. The trackers are moved, as far as possible, in the frontal plane of the user, so as to obtain the maximum value of the length Lt. Then, the length L4 between the left and right shoulders is computed with the following formula:

$$L4=\max(Lt)-2\times(L3+L1)$$

Alternatively, the length of the hand L1 might have been previously computed for both sides of the user (L1*l*=length of the left hand and L1*r*=length of the right hand) and the length of the arm L3 might have been previously computed for both sides of the user (L3*l*=length of the left arm and L3*r*=length of the right arm).

In that case, the length L4 between the left and right shoulders is computed with the following formula:

$$L4=\max(Lt)-(L1l+L1r+L3l+L3r)$$

Considering that each of the steps S1-S4 are carried out on approximately one thousand points, with a refresh rate of 90 Hz, the full estimation of the dimensions of the upper limb lasts less than one minute, which is very quick compared to the techniques using magnetic and/or optical markers.

In an optional preliminary step, before step a) of S1, the user USR may be prompted to input his size. Therefore, a very rough estimation of the length of each member could be displayed at the beginning of steps S1-S4, before computing a dimension of a bone or set of bones based on the estimated center of rotation.

The aforementioned method could also be implemented for measuring dimensions of the lower limb of a user, by means of trackers which could be borne by the foot. The articulated joints would be the ankle, the knee, and the hip.

The inventive method can be performed by a suitably-programmed general-purpose computer or virtual reality system, possibly including a computer network, storing a suitable program in non-volatile form on a computer-readable medium such as a hard disk, a solid state disk or a CD-ROM and executing said program using its microprocessor(s) and memory.

Figure 7:
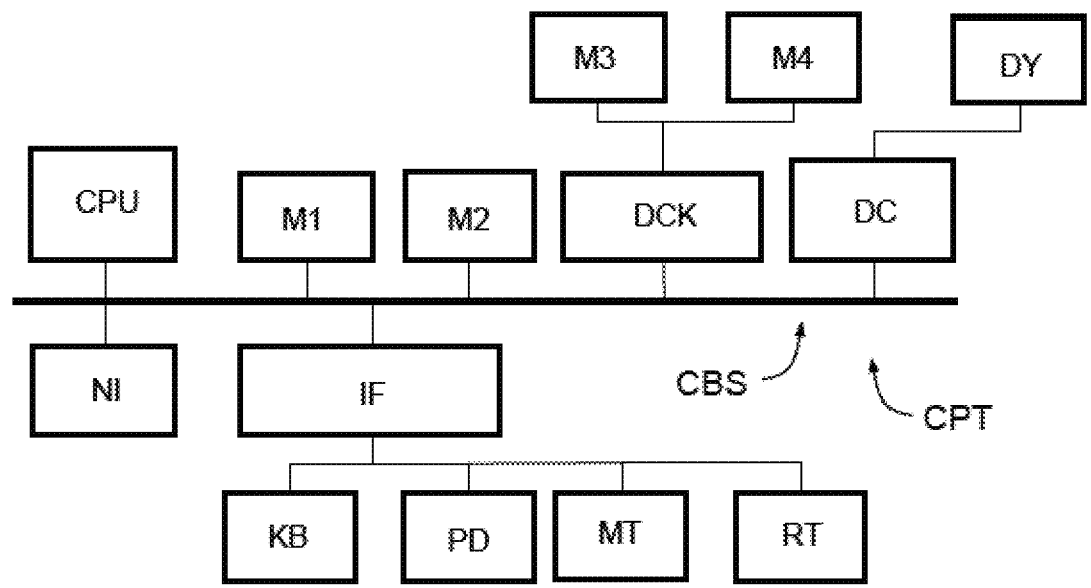
FIG. 7, a computer environment which is adapted to carry out the method according to the disclosure.

A computer CPT suitable for carrying out a method according to an exemplary embodiment is described with reference to FIG. 7. In FIG. 7, the computer CPT includes a Central Processing Unit CPU which performs the method step described above while running an executable program, i.e. a set of computer-readable instructions, stored in a memory device such as RAM M1 or ROM M2 or hard disk drive (HDD) M3, DVD/CD drive M4, or stored remotely.

The claimed invention is not limited by the form of the computer-readable media on which the computer-readable instructions and/or the data structure of the inventive process are stored. For example, the instructions and files can be stored on CDs, DVDs, in FLASH memory, RAM, ROM, PROM, EPROM, EEPROM, hard disk or any other information processing device with which the computer communicates, such as a server or computer. The program and the files can be stored on a same memory device or on different memory devices.

Further, a computer program suitable for carrying out the inventive method can be provided as a utility application, background daemon, or component of an operating system, or combination thereof, executing in conjunction with the Central Processing Unit CPU and an operating system such as Microsoft VISTA, Microsoft Windows 10, UNIX, Solaris, LINUX, Apple MAC-OS and other systems known to those skilled in the art.

The Central Processing Unit CPU can be a Xenon processor from Intel of America or an Opteron processor from AMD of America, or can be other processor types, such as a Freescale ColdFire, IMX, or ARM processor from Freescale Corporation of America. Alternatively, the CPU can be a processor such as a Core2 Duo from Intel Corporation of America, or can be implemented on an FPGA, ASIC, PLD or using discrete logic circuits, as one of ordinary skill in the art would recognize. Further, the Central Processing Unit can be implemented as multiple processors cooperatively working to perform the computer-readable instructions of the inventive processes described above.

The virtual reality system in FIG. 7 also includes a network interface NI, such as an Intel Ethernet PRO network interface card from Intel Corporation of America, for interfacing with a network, such as a local area network (LAN), wide area network (WAN), the Internet and the like. The virtual reality system further includes a head mounted display device HMD having a head tracking device HED. A general purpose I/O interface IF interfaces with trackers (RT, MT). The trackers (MT, RT) may be part of a virtual reality system, for example the "HTC Vive"™ virtual reality system. Each wireless handheld controller of the virtual reality system comprises a tracker (reference tracker or mobile tracker). Tracking of the handheld controller may be done in different ways: through cooperating with base stations, by surface detection, markers, environmental recognition, gyroscopic control units, computer vision.

The display, the keyboard and the pointing device, together with the display controller and the I/O interfaces, form a graphical user interface, used by the user to provide input commands and by the computer for displaying the 3D objects.

Disk controller DKC connects HDD M3 and DVD/CD M4 with communication bus CBS, which can be an ISA, EISA, VESA, PCI, or similar, for interconnecting all of the components of the computer.

Any method steps described herein should be understood as representing modules, segments, or portions of code which include one or more executable instructions for implementing specific logical functions or steps in the process, and alternate implementations are included within the scope of the exemplary embodiment.

The claimed invention is:

1. A method for locating a center of rotation of an articulated joint connecting two bones or set of bones of an upper or lower limb of a user, comprising:
    a) simultaneously acquiring 3D positions of the bone or set of bones during a series of repetitive movements of sweeping one of the two bones or set of bones around the articulated joint by the user, thereby obtaining a 3D cloud of points;
    b) computing, in a 3D searching space comprising a 3D position of a termination of a second bone or set of bones, a point referred to as a center point being a searching point of the 3D searching space for which a standard deviation is the lowest considering a set of distances between the searching point and each point of the 3D cloud of points;
    c) transforming the 3D cloud of points into a single plane for all the points of the 3D cloud of points; and
    d) projecting the center point on said plane, thereby obtaining the center of rotation of the joint,
    wherein in step a), the series of repetitive movements are performed while the user is holding a first one of two hand-held trackers, referred to as mobile tracker, a second one of the two hand-held trackers, referred to as reference tracker, being maintained against a termination of the second bone or set of bones, and
    wherein step b) includes subs-steps of recursively subdividing the 3D searching space by:
    b1) defining the 3D searching space as a cube of predefined edge length, and which is centered on the 3D position of the reference tracker, referred to as reference point,
    b2) receiving, from the user, an input identifying a set of points of the cube constituting, with said reference point, a set of searching points,
    b3) for each searching point, computing the distance between said searching point and each point of the 3D cloud of pints, and deriving a standard deviation for each searching point,
    b4) identifying, among the set of searching points, at least one searching point, for which standard deviation is the lowest, and
    b5) reiterate steps b1), b2), b3) and b4) by also halving the edge length of the cube and centering the cube on the identified searching point, until the edge length of the cube is lower or equal to a predefined threshold, the center point corresponding then to the identified searching point.

2. The method according to claim 1, wherein, in step b2), the cube is subdivided into eight smaller cubes, and the set of searching points includes the reference point or the identified searching point, centers of the smaller cubes, centers of squares of two adjacent smaller cubes, and the middle points of the edge of two adjacent smaller cubes.

3. The method according to claim 1, wherein step c) includes sub-steps of:

c1) computing a covariance matrix of points of the 3D cloud of points;

c2) computing eigenvalues and eigenvectors of the covariance matrix;

c3) constructing a rectangular bounding box enclosing the 3D cloud of points, the orientation of a bounding box corresponding to the eigenvectors, dimensions of the bounding box corresponding to the eigenvalues;

c4) computing a geometry center of the bounding box; and c5) constructing the plane which is defined by two eigenvectors which have the biggest eigenvalues and which passes through the geometry center of the bounding box.

4. The method according to claim 1, wherein, in step a), the acquired 3D positions are stored in frames, each frame comprising a predefined number of 3D positions, and steps b), c) and d) are implemented for all the frames whenever a new frame has been acquired.

5. The method according to claim 4, further comprising:
storing the 3D position of a reference tracker for each implementation of steps a), b), c) and d); and
computing a mean of the 3D positions of the reference tracker, and
discarding a corresponding frame if the 3D position of the reference tracker differs from the mean of the stored 3D positions of the reference tracker from more than a predefined value,
wherein:
in step a), the series of repetitive movements are performed while the user is holding a first one of two hand-held trackers, referred to as mobile tracker, a second one of the two hand-held trackers, referred to as reference tracker, being maintained against a termination of the second bone or set of bones.

6. The method according to claim 4, comprising discarding a frame if, in step c2), it is determined that there is no single eigenvalue which is smaller than others.

7. The method according to claim 1, comprising a step of transmitting in real time to the user an indication of the minimum standard deviation.

8. A non-transitory computer-readable data-storage medium containing computer-executable instructions to cause a computer system to carry out the method for locating the center of rotation of the articulated joint connecting two bones or set of bones of the upper or lower limb of the user according to claim 1.

9. A method for estimating dimensions of an upper limb of a user, comprising:
computing a length of a hand based on a distance between a computed location of the center of rotation of a wrist and the location of an origin of a mobile tracker;
computing the length of a forearm based on the distance between the computed location of the center of rotation of the wrist and the computed location of the center of rotation of an elbow;
computing the length of an upper arm and forearm based on the distance between the computed location of the center of rotation of the wrist and the computed location of the center of rotation of a shoulder; and
computing the length between left and right shoulders based on the length of the upper arm and forearm, the length of the hand, and the maximum distance between a reference tracker and the mobile tracker when each of them are hold in a different hand of the user, and waved in a frontal plane of the user with the arms stretched.

10. A method for locating a center of rotation of an articulated joint connecting two bones or set of bones of an upper or lower limb of a user, comprising:

a) simultaneously acquiring 3D positions of the bone or set of bones during a series of repetitive movements of sweeping one of the two bones or set of bones around the articulated joint by the user, thereby obtaining a 3D cloud of points;

b) computing, in a 3D searching space comprising a 3D position of a termination of a second bone or set of bones, a point referred to as a center point being a searching point of the 3D searching space for which a standard deviation is the lowest considering a set of distances between the searching point and each point of the 3D cloud of points;

c) transforming the 3D cloud of points into a single plane for all the points of the 3D cloud of points; and d) projecting the center point on said plane, thereby obtaining the center of rotation of the joint, wherein step c) includes sub-steps of:

c1) computing a covariance matrix of points of the 3D cloud of points;

c2) computing eigenvalues and eigenvectors of the covariance matrix;

c3) constructing a rectangular bounding box enclosing the 3D cloud of points, the orientation of a bounding box corresponding to the eigenvectors, dimensions of the bounding box corresponding to the eigenvalues;

c4) computing a geometry center of the bounding box; and c5) constructing the plane which is defined by two eigenvectors which have the biggest eigenvalues and which passes through the geometry center of the bounding box.

11. The method according to claim 10, wherein in step a), the series of repetitive movements are performed while the user is holding a first one of two hand-held trackers, referred to as mobile tracker, a second one of the two hand-held trackers, referred to as reference tracker, being maintained against a termination of the second bone or set of bones.

12. The method according to claim 11, wherein step b) includes subs-steps of recursively subdividing the 3D searching space by:

b1) defining the 3D searching space as a cube of predefined edge length, and which is centered on the 3D position of the reference tracker, referred to as reference point, b2) receiving, from the user, an input identifying a set of points of the cube constituting, with said reference point, a set of searching points, b3) for each searching point, computing the distance between said searching point and each point of the 3D cloud of points, and deriving a standard deviation for each searching point, b4) identifying, among the set of searching points, at least one searching point, for which standard deviation is the lowest, and b5) reiterate steps b1), b2), b3) and b4) by also halving the edge length of the cube and centering the cube on the identified searching point, until the edge length of the cube is lower or equal to a predefined threshold, the center point corresponding then to the identified searching point.

13. The method according to claim 12, wherein, in step b2), the cube is subdivided into eight smaller cubes, and the set of searching points includes the reference point or the identified searching point, centers of the smaller cubes, centers of squares of two adjacent smaller cubes, and the middle points of the edge of two adjacent smaller cubes.

14. The method according to claim 10, wherein, in step a), the acquired 3D positions are stored in frames, each frame comprising a predefined number of 3D positions, and steps b), c) and d) are implemented for all the frames whenever a new frame has been acquired.

15. The method according to claim 14, further comprising:
storing the 3D position of a reference tracker for each implementation of steps a), b), c) and d); and
computing a mean of the 3D positions of the reference tracker, and
discarding a corresponding frame if the 3D position of the reference tracker differs from the mean of the stored 3D positions of the reference tracker from more than a predefined value,
wherein:
in step a), the series of repetitive movements are performed while the user is holding a first one of two hand-held trackers, referred to as mobile tracker, a second one of the two hand-held trackers, referred to as reference tracker, being maintained against a termination of the second bone or set of bones.

16. The method according to claim 14, further comprising discarding a frame if, in step c2), it is determined that there is no single eigenvalue which is smaller than others.

17. The method according to claim 10, further comprising a step of transmitting in real time to the user an indication of the minimum standard deviation.

18. A non-transitory computer-readable data-storage medium containing computer-executable instructions to cause a computer system to carry out the method for locating the center of rotation of the articulated joint connecting two bones or set of bones of the upper or lower limb of the user according to claim 10.

19. A device comprising:
a processor coupled to a non-transitory memory,
wherein the memory stores computer-executable instructions to cause the computer system to locate a center of rotation of an articulated joint connecting two bones or set of bones of an upper or lower limb of a user by the processor being configured to:
a) simultaneously acquire 3D positions of the bone or set of bones during a series of repetitive movements of sweeping one of the two bones or set of bones around the articulated joint by the user, thereby obtaining a 3D cloud of points;
b) compute, in a 3D searching space comprising a 3D position of a termination of a second bone or set of bones, a point referred to as a center point being a searching point of the 3D searching space for which a standard deviation is the lowest considering a set of distances between the searching point and each point of the 3D cloud of points;
c) transform the 3D cloud of points into a single plane for all the points of the 3D cloud of points; and
d) project the center point on said plane, thereby obtaining the center of rotation of the joint,
wherein in a), the series of repetitive movements are performed while the user is holding a first one of two hand-held trackers, referred to as mobile tracker, a second one of the two hand-held trackers, referred to as reference tracker, being maintained against a termination of the second bone or set of bones, and
wherein in b) the processor is further configured to recursively subdivide the 3D searching space by the processor being configured to:
b1) define the 3D searching space as a cube of predefined edge length, and which is centered on the 3D position of the reference tracker, referred to as reference point,
b2) receive, from the user, an input identifying a set of points of the cube constituting, with said reference point, a set of searching points,
b3) for each searching point, compute the distance between said searching point and each point of the 3D cloud of points, and derive a standard deviation for each searching point,
b4) identify, among the set of searching points, at least one searching point, for which standard deviation is the lowest, and
b5) reiterate steps b1), b2), b3) and b4) by also halving the edge length of the cube and centering the cube on the identified searching point, until the edge length of the cube is lower or equal to a predefined threshold, the center point corresponding then to the identified searching point.

20. A device comprising:
a processor coupled to a non-transitory memory,
wherein the memory stores computer-executable instructions to cause the computer system to locating a center of rotation of an articulated joint connecting two bones or set of bones of an upper or lower limb of a user by the processor being configured to:
a) simultaneously acquire 3D positions of the bone or set of bones during a series of repetitive movements of sweeping one of the two bones or set of bones around the articulated joint by the user, thereby obtaining a 3D cloud of points;
b) compute, in a 3D searching space comprising a 3D position of a termination of a second bone or set of bones, a point referred to as a center point being a searching point of the 3D searching space for which a standard deviation is the lowest considering a set of distances between the searching point and each point of the 3D cloud of points;
c) transform the 3D cloud of points into a single plane for all the points of the 3D cloud of points; and
d) project the center point on said plane, thereby obtaining the center of rotation of the joint,
wherein in c) the processor is further configured to:
c1) compute a covariance matrix of points of the 3D cloud of points;
c2) compute eigenvalues and eigenvectors of the covariance matrix;
c3) construct a rectangular bounding box enclosing the 3D cloud of points, the orientation of a bounding box corresponding to the eigenvectors, dimensions of the bounding box corresponding to the eigenvalues;
c4) compute a geometry center of the bounding box; and
c5) construct the plane which is defined by two eigenvectors which have the biggest eigenvalues and which passes through the geometry center of the bounding box.

* * * * *